United States Patent [19]

Saad

[11] Patent Number: 5,725,478
[45] Date of Patent: Mar. 10, 1998

[54] METHODS AND APPARATUS FOR PROVIDING SUCTION AND/OR IRRIGATION IN A RIGID ENDOSCOPE WHILE MAINTAINING VISUAL CONTACT WITH A TARGET AREA THROUGH THE ENDOSCOPE

[76] Inventor: Saad A. Saad, 3 Kimball Turn, Holmdel, N.J. 07733

[21] Appl. No.: 615,100

[22] Filed: Mar. 14, 1996

[51] Int. Cl.$^6$ ...................................................... A61B 1/12
[52] U.S. Cl. ........................... 600/157; 600/156; 600/158; 600/159; 600/169
[58] Field of Search ........................ 600/101, 104, 600/121, 123, 153, 156, 157, 158, 159, 169; 604/27, 35, 283, 284, 902; 433/95

[56] References Cited

U.S. PATENT DOCUMENTS

| | | | |
|---|---|---|---|
| 3,791,379 | 2/1974 | Storz | 600/158 |
| 3,924,608 | 12/1975 | Mitsui | 128/2 |
| 4,146,019 | 3/1979 | Bass et al. | 128/6 |
| 4,617,915 | 10/1986 | Arakawa | 128/4 |
| 4,735,194 | 4/1988 | Stiegmann | 128/6 |
| 5,027,792 | 7/1991 | Mever | 600/156 X |
| 5,167,220 | 12/1992 | Brown | 600/156 X |
| 5,170,774 | 12/1992 | Heckele | 128/4 |
| 5,244,459 | 9/1993 | Hill | 604/33 |
| 5,254,083 | 10/1993 | Gentelia et al. | 604/902 X |
| 5,320,630 | 6/1994 | Ahmed | 606/140 |
| 5,329,940 | 7/1994 | Adair | 128/200 |
| 5,333,603 | 8/1994 | Schuman | 128/7 |
| 5,347,992 | 9/1994 | Pearlman et al. | 128/4 |

OTHER PUBLICATIONS

Stephen L. Gans, M.D., Series Editor, *The Pediatric Airway*, "The Principles and Practice of the Pediatric Surgical Specialties", p. 53.

Reddick/Saye Lav–1™, sales brochure for "Laser Delivery Channel, Irrigation and Aspiration Probe for Laparoscopic Surgery", (2 pages), Mectra Labs, Inc.

Lap Vacu–Irrigator™, Laparoscopic Irrigation/Aspiration Device, Sales Brochure, (2 pages), Mectra Labs™, Inc.

*Primary Examiner*—Beverly M. Flanagan
*Attorney, Agent, or Firm*—Michaelson & Wallace; Michael P. Straub; Peter L. Michaelson

[57] ABSTRACT

Methods and apparatus for providing suction and/or irrigation in rigid endoscopes used for, e.g., bronchoscopy, esphagoscopy, and sigmoidoscopy are described. The described methods and apparatus permit a user of the endoscope to maintain visual contact with a target area being viewed though the endoscope during suction/irrigation procedures. In accordance with the present invention, the antifog port of a known rigid endoscope assembly is coupled to a suction/irrigation apparatus as opposed to being plugged or coupled to an antifog fluid source. The antifog port is thereby converted into a suction/irrigation port. By providing suction/irrigation via the antifog port, the need to remove the telescope to perform suction and/or the need to use an instrument incorporating a suction channel is eliminated. The suction/irrigation apparatus of the present invention includes an extension tube, a syringe, a valve, e.g., a two way stop cock, and a connecting tube. The stop cock is used to selectively couple either the source of the irrigation fluids, e.g., the syringe, or a suction device to the antifog port of the rigid endoscope. The syringe includes calibration marks and is filled with an irrigation fluid, e.g., saline fluid. The extension tube is used to position the two way stop cock and syringe a sufficient distance away from the rigid endoscope so that it can be operated by an assistant without interfering with the person using the endoscope.

9 Claims, 4 Drawing Sheets

METHODS AND APPARATUS FOR PROVIDING SUCTION AND/OR IRRIGATION IN A RIGID ENDOSCOPE WHILE MAINTAINING VISUAL CONTACT WITH A TARGET AREA THROUGH THE ENDOSCOPE

FIELD OF THE INVENTION

The present invention is directed to providing suction and/or irrigation in rigid endoscopes and, more particularly, to methods and apparatus for providing suction and/or irrigation in, e.g., rigid endoscopes used for bronchoscopy, esophagoscopy, and sigmoidoscopy which permit the user of the endoscope to maintain visual contact with a target being viewed though the endoscope.

BACKGROUND OF THE INVENTION

An endoscope is an instrument which is used to visualize the interior of a body cavity or organ. There are many different types of endoscopes. For example, there are flexible endoscopes which frequently incorporate fiber optic lines. The fiber optic lines are used for viewing a target area or for providing laser energy to a target area. In addition to fiber optic lines, one or more lumens may be molded directly into the flexible endoscope. In such endoscopes, the lumens are integral components of the endoscope. The lumens of flexible endoscopes may be used for providing suction and/or irrigation fluids to a target area. Because the lumens used for this purpose are part of the endoscope, they do not interfere with the presence of the optical endoscope components. Accordingly, it is possible to view the target area using the flexible endoscope at the same time the target area is suctioned or irrigated.

In addition to incorporating suction/irrigation lumens into the body of a flexible endoscope, suction/irrigation controls will frequently be incorporated directly into the handle of a flexible endoscope to permit an endoscope user to the hold the endoscope with one hand and control the endoscope's suction/irrigation capabilities with the other hand.

Rigid endoscopes, unlike flexible endoscopes, tend to be constructed from a plurality of rigid components, e.g., metal tubular components which are designed to fit inside one another. Because of the rigid tubular design of such endoscopes, the molding of suction and/or irrigation lumens into the endoscope body is difficult. For this reason, rigid endoscopes tend not to include integral lumens for irrigation and/or suction purposes.

Referring now to FIG. 1 the components of a known rigid endoscope, commonly used for performing bronchoscopy esophagoscopy, and sigmoidoscopy are illustrated. The known rigid endoscope comprises three main components: 1) a straight forward telescope 10; 2) an antifog tube 20 and 3) a tubular sheath instrument channel 30.

The telescope 10 includes a distal fiber light connection 11 through which light may be supplied to the tip of the telescope 10. The antifog tube 20 includes a telescope port 23, a tubular antifog port 21 and a telescope lock 22. The antifog port 21 is frequently plugged, i.e., not used, or coupled to a source of an antifog air which is directed to the tip of the endoscope to prevent the lens of the telescope 10 from fogging. The tubular sheath instrument channel 30 includes a prismatic light deflector opening 31, an instrument port 33 and an antifog tube port 32.

A prismatic light deflector 34 can be coupled to the prismatic light deflector opening 31 and to a proximal prism light.

Referring now to FIG. 2, the components of the known rigid endoscope are illustrated assembled together for use in a known manner to form the endoscope assembly 200. As illustrated, the telescope 10 is inserted into the telescope opening 23 of the antifog tube 20. The antifog tube 20 and telescope 10 are coupled to the antifog tube opening 32 of the tubular sheath instrument channel 30. A distal prism light 60 is coupled to the prismatic light deflector opening 31 by the prismatic light deflector 34. A light transmitting cable 52 is coupled to the fiber light connection 11.

As illustrated in FIG. 2, the forceps 40 of FIG. 1 may be inserted into the instrument channel opening 33 so that the tip of the forceps 40 protrudes out the tip of the endoscope assembly 200.

During an endoscopic procedure, a suction tube 50, illustrated in FIG. 1, may be used with the known rigid endoscope assembly 200. However, to use the suction tube 50, the telescope 10 and the antifog tube 20 must be removed from the endoscope assembly 200 and the suction tube 50 inserted in the opening 32 of the tubular sheath instrument channel 30 as illustrated in FIG. 3.

Because the telescope 10 must be removed for insertion of the suction tube 50, when suction is to be performed using the known rigid endoscope assembly 200, the user of the endoscope losses visual contact with the target area that was being viewed through the telescope 10.

Frequently, the known endoscope assembly 200 is used for extracting foreign objects that have been swallowed or inhaled by a patient. As a result of the suction process, a foreign object may change location. Thus, upon removing the suction tube 50 and reinserting the telescope 10, the endoscope user may have to reposition the endoscope assembly 200 to search for the foreign object that shifted during the suction process. This can increase the time and the effort required to perform an extraction procedure.

Irrigation with fluid, e.g., saline fluid through the endoscopic assembly 200 to clear body secretions obstructing the endoscope user's view is generally performed using the same technique used for suction.

In order to permit an operator of a rigid endoscope to perform suction without loosing visual contact with a target area or object, at least one manufacturer has incorporated a suction channel into an instrument, e.g., a pair of forceps. Such an approach to providing suction has the disadvantage of limiting the instruments which can be used with the endoscope assembly to, e.g., those instruments which incorporate a suction channel directly into the instrument. This approach also has the disadvantage of providing a relatively small suction channel since the size of the suction channel is limited to the excess space available in the instrument channel.

In view of the disadvantages of the known methods of providing suction and/or irrigation when using the rigid endoscope components illustrated in FIG. 1, there is a need for a method and apparatus that can be used to provide suction and/or irrigation without requiring the removal of the telescope 10 and the antifog tube 20 and without requiring the use of instruments incorporating a suction channel. It is desirable that such a method and apparatus be inexpensive and easy to implement using readily available medical supplies which may be disposed of after each use. It is also desirable that the suction/irrigation apparatus not require the addition of special handles or other significant and potentially costly modifications to the existing known rigid endoscope.

In order to permit a user of the rigid endoscope to hold the rigid endoscope with one hand and operate an instrument, e.g., foreign body extracting forceps 40 with the other hand, it is desirable that the suction/irrigation controls be located at a distance from the endoscope. The distance should be sufficient to permit an assistant to operate the suction irrigation/controls without interfering with the control of the endoscope and instrument by the person performing the endoscopic procedure.

It is also desirable that irrigation be provided in a controlled manner and, if desired, at a pressure which is greater than the pressure which can easily be obtained from using an elevated fluid bag sometimes used as a source of irrigation fluid.

SUMMARY OF THE PRESENT INVENTION

The present invention is directed to methods and apparatus for providing suction and/or irrigation in rigid endoscopes used for, e.g., bronchoscopy, esophagoscopy and sigmoidoscopy. The methods and apparatus of the present invention permit the user of a rigid endoscope to maintain visual contact with a target area and/or object being viewed though the endoscope during suction/irrigation procedures.

In accordance with one embodiment of the present invention, the antifog port 21 of the known rigid endoscope assembly illustrated in FIG. 2, is coupled to a suction/irrigation apparatus as opposed to being plugged or coupled to an antifog air source. The antifog port of the endoscope assembly is thereby converted into a suction/irrigation port. In such an embodiment, the area between the outer surface of the tubular rigid telescope 10 and the inner surface of the antifog tube 20 serves as the suction irrigation channel. By providing suction/irrigation via the existing antifog port, the need to remove the telescope 10 to perform suction, and/or the need to use an instrument incorporating a suction channel, is eliminated. Because the position of the telescope remains unchanged when performing suction/irrigation in accordance with the present invention, visual contact with a target area or a foreign object can be maintained at all times. In the event that a foreign object shifts its position during the suction or irrigation process, the endoscope operator can adjust the endoscope position as the object moves to avoid loosing visual contact with the object and the need to repeatedly search for the object.

In addition to allowing an endoscope operator to maintain visual contact with a target area or object during the suction/irrigation process, the present invention has the advantage that it can be used with the known rigid endoscopes currently used for, e.g., bronchoscopy, esophagoscopy, and sigmoidoscopy without requiring alterations to the components of the known rigid endoscope.

The suction/irrigation apparatus of the present invention includes an extension tube, a connecting tube, a syringe, and a two way valve, e.g., a stop cock. The stop cock includes three ports.

In accordance with the present invention a first end of the extension tube is coupled to the antifog port of the known rigid endoscope assembly's antifog tube. A second end of the extension tube is coupled to the first port of a two way stop cock.

A second port of the two way stop cock is coupled to a suction apparatus by way of the connecting tube while a third port of the two way stop cock is coupled to a syringe which is filled with an irrigation fluid, e.g., saline solution.

In accordance with the present invention, the two way stop cock is used to selectively couple either the suction device or source of the irrigation fluid to the extension tube. When suction is required, the position of the stop cock is adjusted so that the suction device is coupled to the antifog port via the extension tube. When irrigation is required, the position of the stop cock is adjusted so that the source of the irrigation fluid is coupled via the extension tube to the antifog port.

In accordance with one embodiment of the present invention, the stop cock is labeled to indicate to an operator which position a handle of the stop cock must be in to provide suction and which position it must be in to provide irrigation.

Because the source of irrigation fluid is a syringe, no irrigation fluid is provided without an operator providing pressure to the plunger of the syringe. Accordingly, the stop cock may be left in the irrigation position without concern for irrigation fluids being unintentionally supplied to the endoscope assembly. Use of a syringe as the source of irrigation fluids offers more control, in terms of delivery pressure and quantity, than is possible using, e.g., an elevated bag, as the irrigation fluid source.

Using the connecting tube to couple the stop cock to a source of suction permits an assistant to control suction to clear the view for the endoscopic user at the end of the telescope.

Using the extension tube to couple the stop cock to the antifog port, permits an assistant to control the delivery of irrigation fluids and suction from a sufficient distance from the endoscope assembly so as not to interfere with the person performing the endoscopic procedure.

Because the suction/irrigation apparatus of the present invention comprises relatively inexpensive components it can be implemented as a disposable single use device. Furthermore, it has the advantage of not requiring difficult to find or custom made components.

The above described features and advantages of the present invention along with others are discussed in detail below.

DETAILED DESCRIPTION

Figure 1:
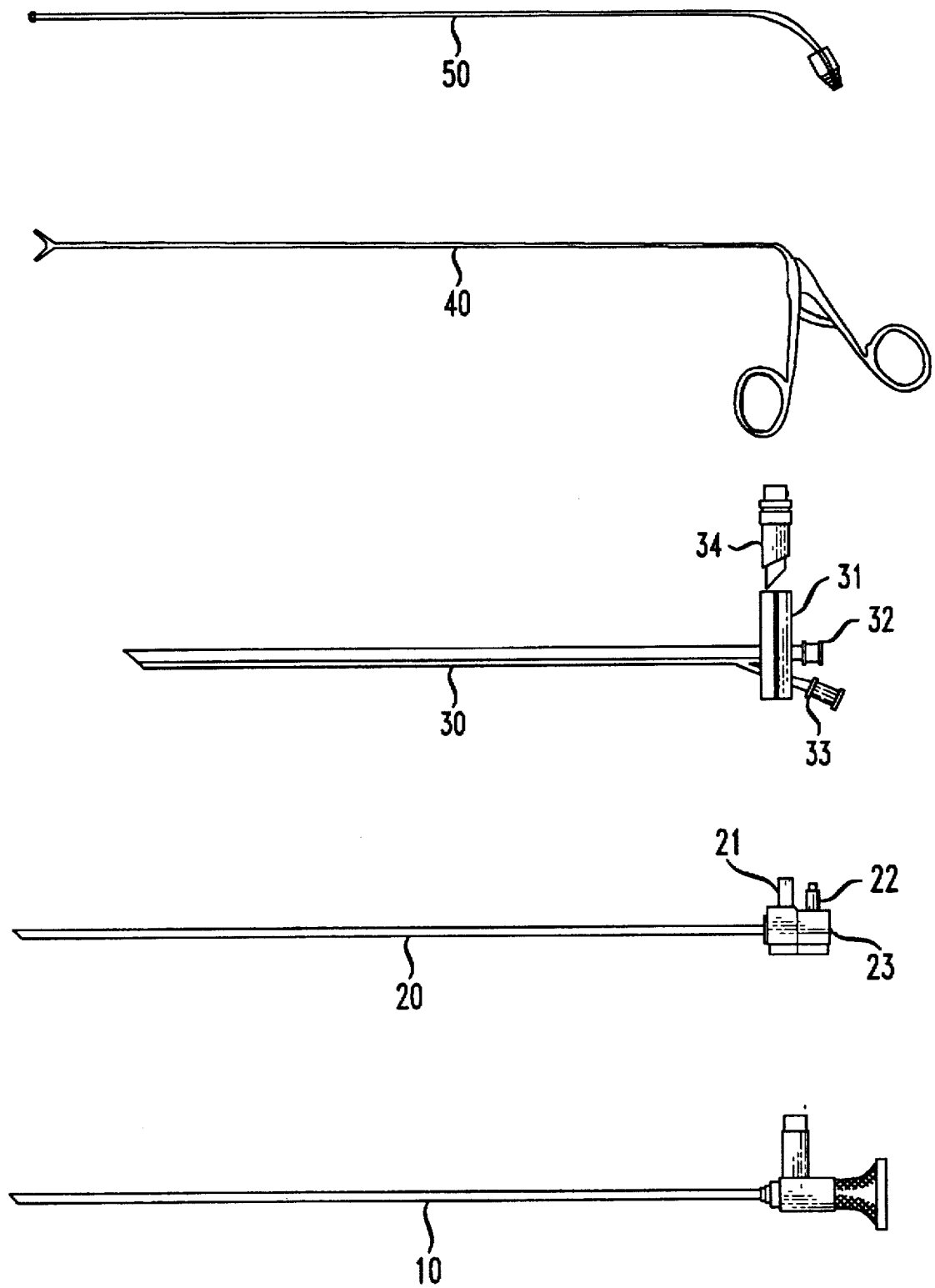
FIG. 1 illustrates a plurality of known rigid endoscope components in addition to a suction device and forceps suitable for use with the known rigid endoscope components.
Figure 2:
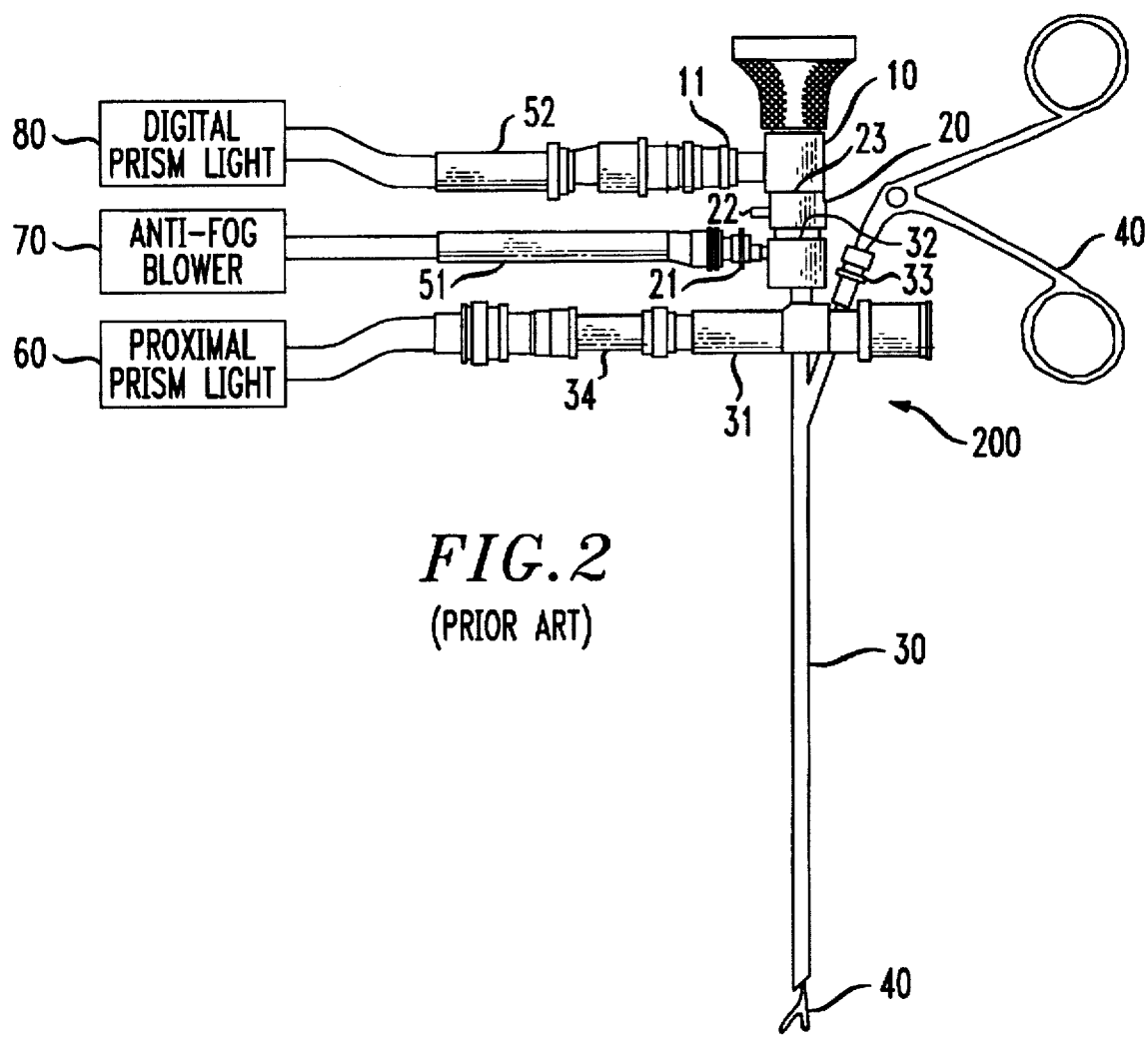
FIG. 2 illustrates the endoscope components of FIG. 1 assembled together, as is known in the art.
Figure 3:
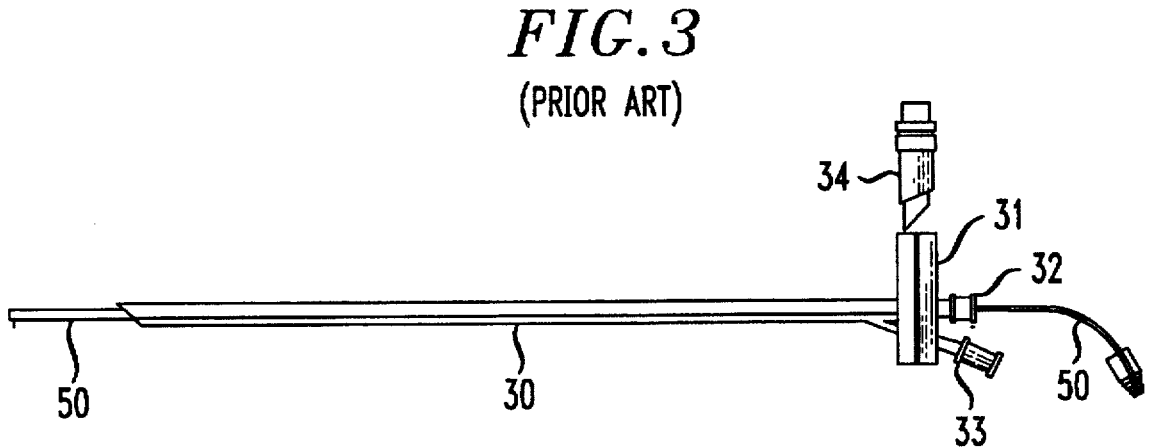
FIG. 3 illustrates the known method of performing suction by inserting a suction tube into the tubular sheath instrument channel after removing the telescope and the antifog tube.
Figure 4:
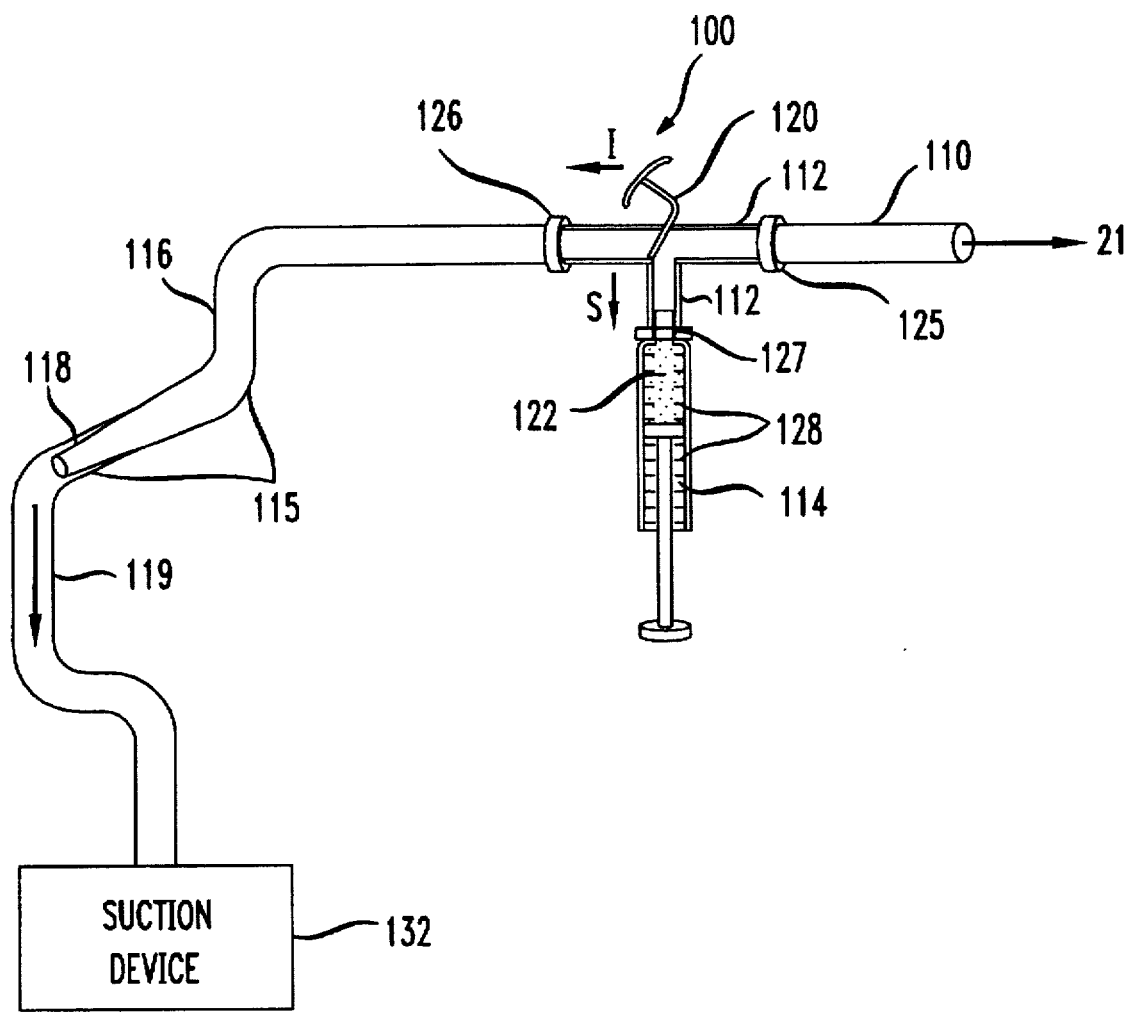
FIG. 4 illustrates a suction/irrigation apparatus implemented in accordance with one embodiment of the present invention.
Figure 5:
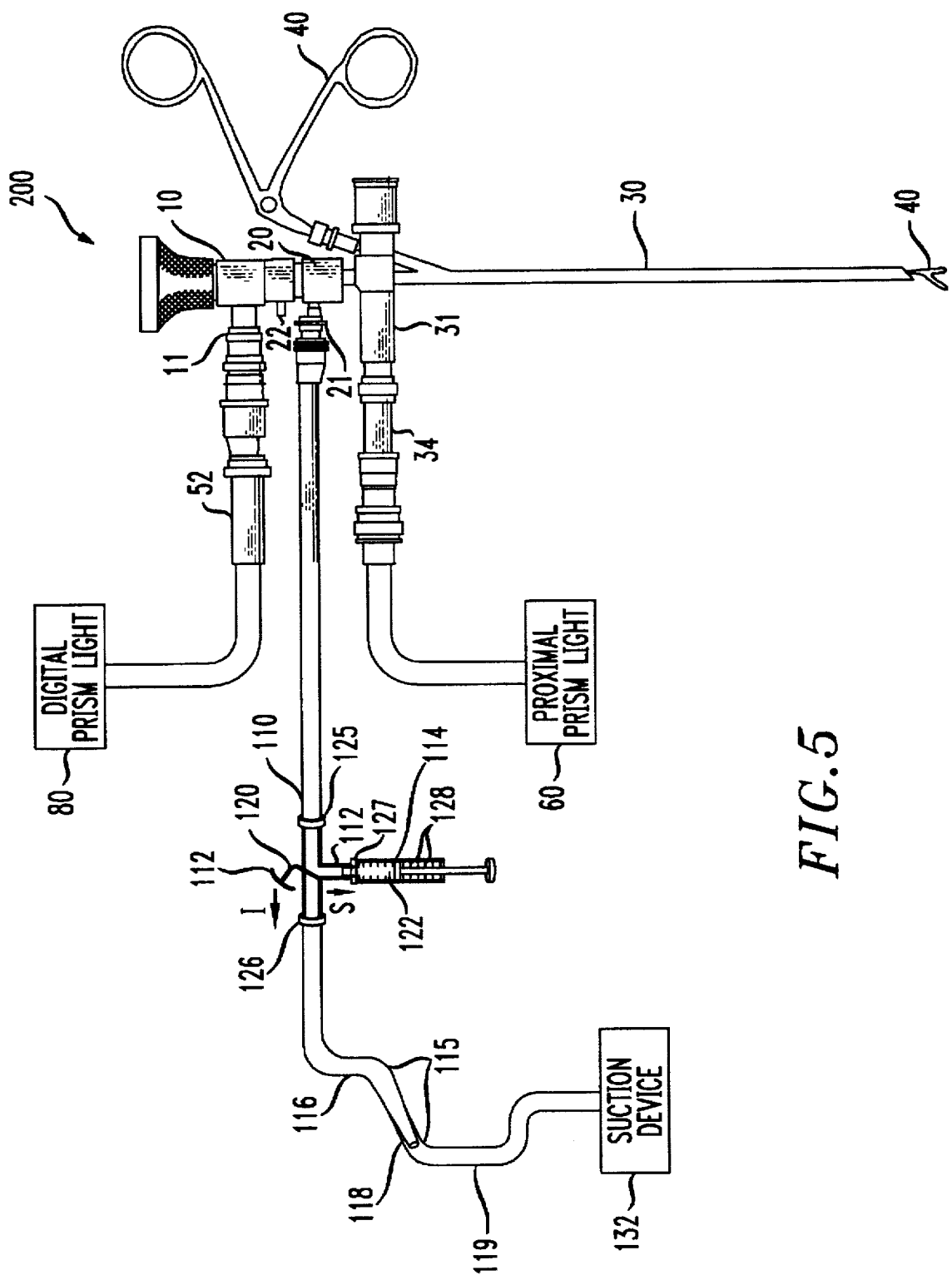
FIG. 5 illustrates the suction irrigation apparatus of FIG. 4, connected to a known rigid endoscope assembly.

Referring now to FIG. 4, there is illustrated a suction/irrigation apparatus 100 implemented in accordance with the present invention. As illustrated in FIG. 5, the apparatus 100 may be coupled to a known rigid endoscope assembly 200 of the type described in regard to FIG. 2. The rigid endoscope and suction/irrigation apparatus of the present invention are well suited for performing bronchoscopy, esophagoscopy, and/or sigmoidoscopy.

The suction/irrigation apparatus of the present invention, generally indicated by the reference numeral 100, comprises an extension tube 110, a syringe 114, a two way valve 112, e.g., a stop cock, and a connecting tube 115. The connecting tube 115 may comprise a first section 116 having a first internal diameter suitable for connecting the connecting tube 115 to the stop cock 112, and a second tapered section 118 suitable for coupling the connecting tube 115 to a suction tube 119 of the suction device 132. The connecting tube 115 may be a suction catheter which has a tapered end 118. The outside diameter of the tapered end 118 permits it to be inserted inside the suction tube 119. As will be apparent to one of ordinary skill in the art these apparatus components have the advantage of being inexpensive and readily available from most medical supply stores.

In accordance with the present invention, rather than plug the antifog port 21 of the antifog tube 20 of the known rigid endoscope assembly 200, or connect it to a source of an anti-fog air 70, the port 21 is coupled to the suction irrigation apparatus 100 of the present invention. The antifog port 21 is thereby converted into a suction/irrigation port. In such an embodiment, the area between the outer surface of the tubular rigid telescope 10 and the inner surface of the antifog tube 20 serves as the suction irrigation channel. By providing suction/irrigation via the antifog port 21, the need to remove the telescope to perform suction and/or the need to use an instrument incorporating a suction channel is eliminated.

Because the position of the telescope 10 is not changed as a result of the suction/irrigation process performed in accordance with the present invention, visual contact with a target area or foreign object can be maintained throughout an endoscopic procedure. In the event that a foreign object shifts its position during the suction/irrigation process, the endoscope operator can adjust the position of the endoscope assembly 200 as the object moves. In this manner an operator can avoid loosing visual contact with an object being viewed and the need to repeatedly search for the object.

In accordance with the present invention as illustrated in FIG. 5, a first end of the extension tube 110 is coupled to the antifog port 21 of the endoscope assembly 200. A second end of the extension tube 110 is coupled to a first port 125 of the two way stop cock 112. The extension tube 110 and connecting tube 115 may comprise a clear plastic material through which the passage of fluids or other material can be seen.

The stop cock 112 includes a total of three ports 125, 126, 127 and a valve which is located inside the stop cock. The valve is used to couple one of the second 126 and third 127 ports to the first 125 port at any given time. An arrow 120 on a handle of the stop cock 112 is used as an indicator of the connection that is established between the ports as a result of the handle's position. In one embodiment, the stop cock is labeled with an I on the second port 126 and an S on the third port 127. The I is used to indicate the handle position, as indicated by the arrow 120, that is required to provide irrigation fluid to the endoscope assembly. Similarly the S is used to indicate the handle position required to provide suction to the endoscope assembly. To provide either suction or irrigation, the stop cock handle is rotated so that the arrow 120 is aligned with the letter indicator associated with the desired procedure, i.e., suction or irrigation.

The second port 126 of the stop cock 112 is coupled to a suction device 132 by the connecting tube 115. In this manner, suction is supplied to the second port 126 of the stop cock 112. The syringe 114 is coupled to the third port 127 of the stop cock 112. The syringe 114 is filled with an irrigation solution, e.g., a saline solution 122. When irrigation is required, the position of the stop cock 112 is adjusted so that the source of the irrigation fluid, i.e., the syringe 114 is coupled via the extension tube 110 to the antifog port 21.

Because the source of irrigation fluid is the syringe 114, no irrigation fluid is provided without an operator providing pressure to the plunger of the syringe 114. Accordingly, the stop cock 112 may be left in the irrigation position even when irrigation is not required without concern for irrigation fluids being unintentionally supplied to the antifog port 21. Use of the syringe 114 as the source of irrigation fluid offers more control, in terms of delivery pressure and precise quantity, than is possible using, e.g., an elevated bag as the irrigation fluid source. The pressure that can be produced by the syringe 114 is greater than that generally available from an elevated fluid bag. The syringe 114 includes a plurality of calibration marks 128 which facilitate the provision of precise amounts of irrigation fluids.

Using the extension tube 110 to couple the stop cock 112 to the antifog port 21 permits an assistant to control the delivery of irrigation fluids and suction from a sufficient distance, e.g., ¼ of a meter or more, from the endoscope assembly 200, so as not to interfere with the person using the rigid endoscope assembly.

Because the suction/irrigation apparatus 100 of the present invention comprises relatively inexpensive components it can be implemented as a disposable single use device. With current concerns of possibly spreading infectious diseases by reusing medical devices, the low cost and disposability of the suction/irrigation apparatus of the present invention is a highly desirable feature. In addition to low cost, the present invention has the advantage of being suitable for use with rigid endoscopes that are already in wide spread use in the fields of bronchoscopy, esophagoscopy and sigmoidoscopy.

What is claimed is:
1. An endoscopic system, comprising:
   a rigid endoscope including:
      i. a tubular sheath instrument channel;
      ii. an antifog tube including a port, the antifog tube being inserted into the tubular sheath instrument channel; and
      iii. a straight telescope inserted into the antifog tube;
   a suction/irrigation apparatus including:
      i. an extension tube having a first end coupled to the port of the antifog tube;
      ii. a valve having a first, second and third port for selectively coupling one of the second and third ports to the first port, the first port being coupled to a second end of the extension tube;
      iii. a connecting tube coupled to the second port of the valve and adapted for coupling the second port to a suction device; and
      iv. a syringe coupled to the third port of the valve for providing irrigation fluid.
2. The endoscopic system of claim 1, wherein the rigid endoscope is a metallic endoscope suitable for use as a bronchoscope, an esophagoscope, and as a sigmoidoscope.
3. The endoscopic system of claim 2, wherein the valve is a two way stop cock.
4. The endoscopic system of claim 3, further comprising:
   a suction device; and
   wherein the connecting tube includes a suction catheter having a first section which has an internal diameter suitable for connecting the first section to the stop cock and a second tapered section for coupling the connecting tube to the suction device.

5. The endoscopic system of claim 3, wherein the two way stop cock includes a handle and markings which indicate a first handle position for irrigation and a second handle position for suction.

6. The endoscopic system of claim 2, wherein the syringe includes gradations indicative of an amount of fluid in the syringe.

7. The endoscopic system of claim 6, wherein the extension tube is at least ¼ of a meter long.

8. The endoscopic system of claim 7, wherein the extension tube and the connecting tube are made of a clear plastic material.

9. An endoscopic system, comprising:

a suction device;

a rigid bronchoscope including:
   i. a tubular sheath instrument channel having a prismatic light deflector opening, an instrument port and an antifog tube port;
   ii. an antifog tube inserted into the antifog tube port of the tubular sheath instrument channel, the antifog tube including a telescope opening, a tubular antifog input port, and a telescope lock; and
   iii. a straight telescope inserted into the telescope opening of the antifog tube; and a suction/irrigation apparatus including:
   i. an extension tube that is at least ¼ of a meter in length coupled to the tubular antifog port of the antifog tube;
   ii. a two way stop cock having a first, second and third port, a handle and markings, the two way stop cock selectively coupling one of the second and third ports to the first port as a function of the handle position, the markings indicating the handle position which results in suction being provided to the tubular antifog port and the handle position which results in irrigation being provided to the tubular antifog port, the first port being coupled to the tubular antifog port by the extension tube;
   iii. a transparent connecting tube coupled to the second port of the two way stop cock and to the suction device; and
   iv. a syringe having calibration marks on the side of the syringe, coupled to the third port of the valve, the syringe serving as an irrigation fluid source.

\* \* \* \* \*